(12) United States Patent
Jabri et al.

(10) Patent No.: US 7,450,747 B2
(45) Date of Patent: Nov. 11, 2008

(54) SYSTEM AND METHOD FOR EFFICIENTLY CUSTOMIZING AN IMAGING SYSTEM

(75) Inventors: Kadri N. Jabri, Waukesha, WI (US); Grant M. Stevens, Cedarburg, WI (US); Vianney P. Battle, Milwaukee, WI (US); Jianqing Yao, Pewaukee, WI (US); Renuka Uppaluri, Pewaukee, WI (US); Kevin J. Hobert, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1218 days.

(21) Appl. No.: 10/193,835

(22) Filed: Jul. 12, 2002

(65) Prior Publication Data

US 2004/0008900 A1  Jan. 15, 2004

(51) Int. Cl.
*G06K 9/00* (2006.01)
(52) U.S. Cl. .................. 382/132; 382/128; 382/167; 382/224
(58) Field of Classification Search .......... 382/128, 382/129, 131, 132, 162, 167, 224; 358/1.9, 358/5.18–523; 378/97, 154; 715/512
See application file for complete search history.

(56) References Cited

U.S. PATENT DOCUMENTS

| | | | | |
|---|---|---|---|---|
| 4,160,906 A | * | 7/1979 | Daniels et al. | 378/97 |
| 5,531,520 A | * | 7/1996 | Grimson et al. | 382/131 |
| 5,734,915 A | * | 3/1998 | Roewer | 715/512 |
| 5,899,999 A | * | 5/1999 | De Bonet | 707/104.1 |
| 6,175,643 B1 | * | 1/2001 | Lai et al. | 382/131 |
| 6,963,360 B1 | * | 11/2005 | Esquibel et al. | 348/207.99 |
| 6,980,233 B1 | * | 12/2005 | Hirasawa | 348/207.1 |
| 2003/0095147 A1 | * | 5/2003 | Daw | 345/771 |
| 2005/0174591 A1 | * | 8/2005 | Sowinski et al. | 358/1.9 |
| 2005/0185055 A1 | * | 8/2005 | Miller et al. | 348/207.1 |

* cited by examiner

*Primary Examiner*—Matthew C. Bella
*Assistant Examiner*—Ali Bayat
(74) *Attorney, Agent, or Firm*—Fletcher Yoder (57) ABSTRACT

The present technique provides a system and method for efficiently customizing an imaging system, such as a medical diagnostic imaging system. Based on images typically produced by one or more imaging systems, the present technique forms a plurality of image subject matter groups each having a plurality of related image types/views and one representative image type/view. Each customer is then provided with a plurality of predefined image style options for each of the plurality of representative image types/views. The predefined image style selected for each of the plurality of representative image types/views is then applied to each of the plurality of related image types/views in the respective image subject matter group. The imaging system is then automatically customized based on the foregoing predefined image style selections.

58 Claims, 7 Drawing Sheets

SYSTEM AND METHOD FOR EFFICIENTLY CUSTOMIZING AN IMAGING SYSTEM

BACKGROUND OF THE INVENTION

The present technique relates generally to imaging systems, such as medical diagnostic imaging systems. In particular, the present technique provides an efficient system and method for custom configuration of imaging systems based on customer feedback and expertise.

Imaging systems are often used to acquire and process particular types and views of subject matter, such as different views of anatomies in medical diagnostic imaging. For example, each imaging system may be customized to acquire images having a specific appearance or style to accentuate a desired aspect of the subject matter. Each customer also may have different image style preferences, such as different preferences of image contrast, brightness, edge characteristics, resolution, color depth, intensity, and various other image characteristics. If the imaging system produces a video stream, then the customer also may have a variety of image style preferences relating to the video stream, including audio characteristics. Imaging systems generally have a large number of parameters, such as image acquisition and processing parameters, which may be modified to alter the look and quality of the image. Although some of these parameters may be transparent to the user/customer, these parameters are used to customize or tailor the look and quality of the image to the preferences of the customer. Accordingly, the wide variety of imaging applications and customer preferences necessitates considerable customization of each individual imaging system to ensure the desired appearance/style of the images.

The need for customization is particularly apparent in medical diagnostic and imaging systems, which include a number of different modalities. These modalities include computed tomography (CT) systems, x-ray systems (including both conventional and digital or digitized imaging systems), magnetic resonance (MR) systems, positron emission tomography (PET) systems, ultrasound systems, nuclear medicine systems, and so forth. The foregoing imaging systems are invaluable instruments for identifying, diagnosing and treating physical conditions to reduce the need for surgical diagnostic intervention. In many instances, these modalities complement one another and offer the physician a range of techniques for imaging particular types of bones, soft tissue, organs, physiological systems, and so forth. However, each application and system may require different image acquisition and/or processing parameters to accentuate the desired subject matter for diagnosis. Each customer also may have particular preferences for the general appearance or style of the images in each medical diagnostic area, such as different anatomical areas.

In digital x-ray imaging, image processing is generally customized for a particular customer through a lengthy and iterative process involving significant use of trial and error. The image processing parameters for each image view are modified and verified through repeated site visits to ensure customer satisfaction. The foregoing process is repeated for all anatomical views. For example, the customization of a digital x-ray system may involve over 137 iterations of the foregoing process to accommodate the over 137 anatomical views typically produced by the digital x-ray system. In addition to each site having different individual image preferences due to varying clinical focuses/practices, parameters used at one site are not necessarily applicable at another site due to differences in image review workflow (e.g., printed film versus PACS station) and equipment (e.g., different film types, monitors, etc.). As a result, the customization process has to be repeated for every site, yet the experience gained by the person performing the customization at one site does not necessarily carry over to other sites.

Accordingly, a technique is needed for efficiently customizing an imaging system to produce images having the image styles expected for each image type/view.

BRIEF DESCRIPTION OF THE INVENTION

The present technique provides a system and method for efficiently customizing an imaging system, such as a medical diagnostic imaging system. Based on images typically produced by one or more imaging systems, the present technique forms a plurality of image subject matter groups each having a plurality of related image types/views and one representative image type/view. Each customer is then provided with a plurality of predefined image style options for each of the plurality of representative image types/views. The predefined image style selected for each of the plurality of representative image types/views is then applied to each of the plurality of related image types/views in the respective image subject matter group. The imaging system is then automatically customized based on the foregoing predefined image style selections.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

The present technique provides a system and method for efficiently customizing an imaging system, such as a medical diagnostic imaging system. As discussed in detail below, the present technique identifies a plurality of image types/views typically produced by one or more imaging systems, selects a plurality of core image types/views representative of the plurality of image types/views, groups each of the remaining image types/views with one of the core image types/views based on an imaging relationship, and provides each customer with a plurality of image style options for each of the plurality of core image types/views. The present technique then proceeds to configure the imaging system based on a customer's selection of a preferred image style for each of the plurality of core image types/views. Specifically, the preferred image style for each of the plurality of core image types/views is used for all related images in the group with the respective core image type/view. The foregoing image subject matter groups and image styles may be based on clinical expertise, statistical analysis of customer feedback, and any other suitable factors. Accordingly, the use of image subject matter groups and predefined styles expedites the customization of each individual imaging system to the customer's preferences.

Figure 1:
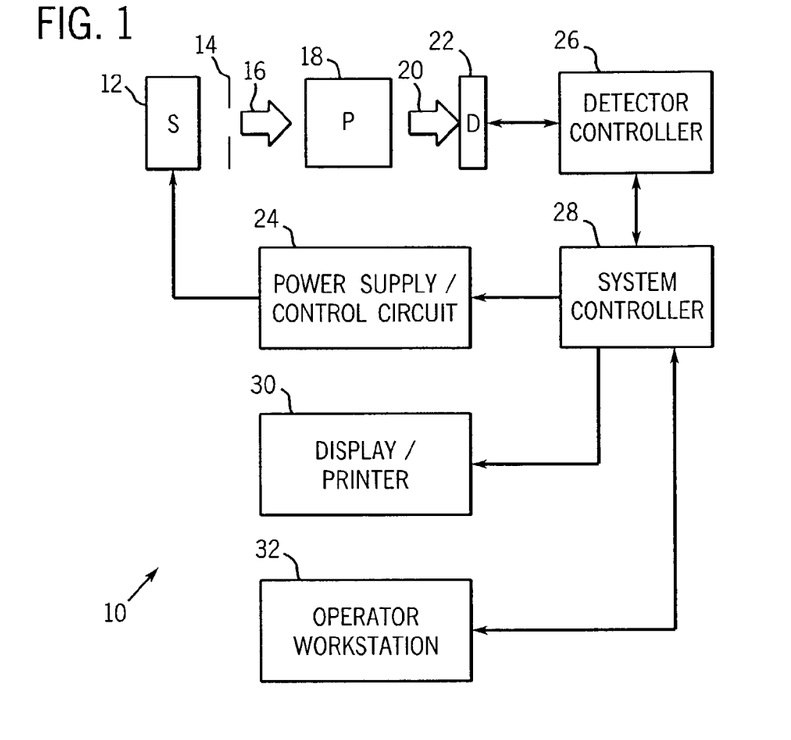
FIG. 1 is a diagrammatical overview of a digital X-ray imaging system in which the present technique may be utilized.

The present technique may be used in any suitable imaging system, including still imaging and video imaging systems. FIG. 1 illustrates diagrammatically an imaging system 10 for acquiring and processing discrete pixel image data. In the illustrated embodiment, the imaging system 10 is a digital X-ray system designed both to acquire original image data and to process the image data for display in accordance with the present technique. However, the imaging system 10 may include any other non-medical or medical imaging systems, such as computed tomography (CT) systems, magnetic resonance (MR) systems, positron emission tomography (PET) systems, ultrasound systems, nuclear medicine systems, and so forth. In the embodiment illustrated in FIG. 1, the imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals, which are acquired and processed to reconstruct an image of the features within the subject.

Source 12 is controlled by a power supply/control circuit 24, which furnishes both power, and control signals for examination sequences. Moreover, detector 22 is coupled to a detector controller 26, which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
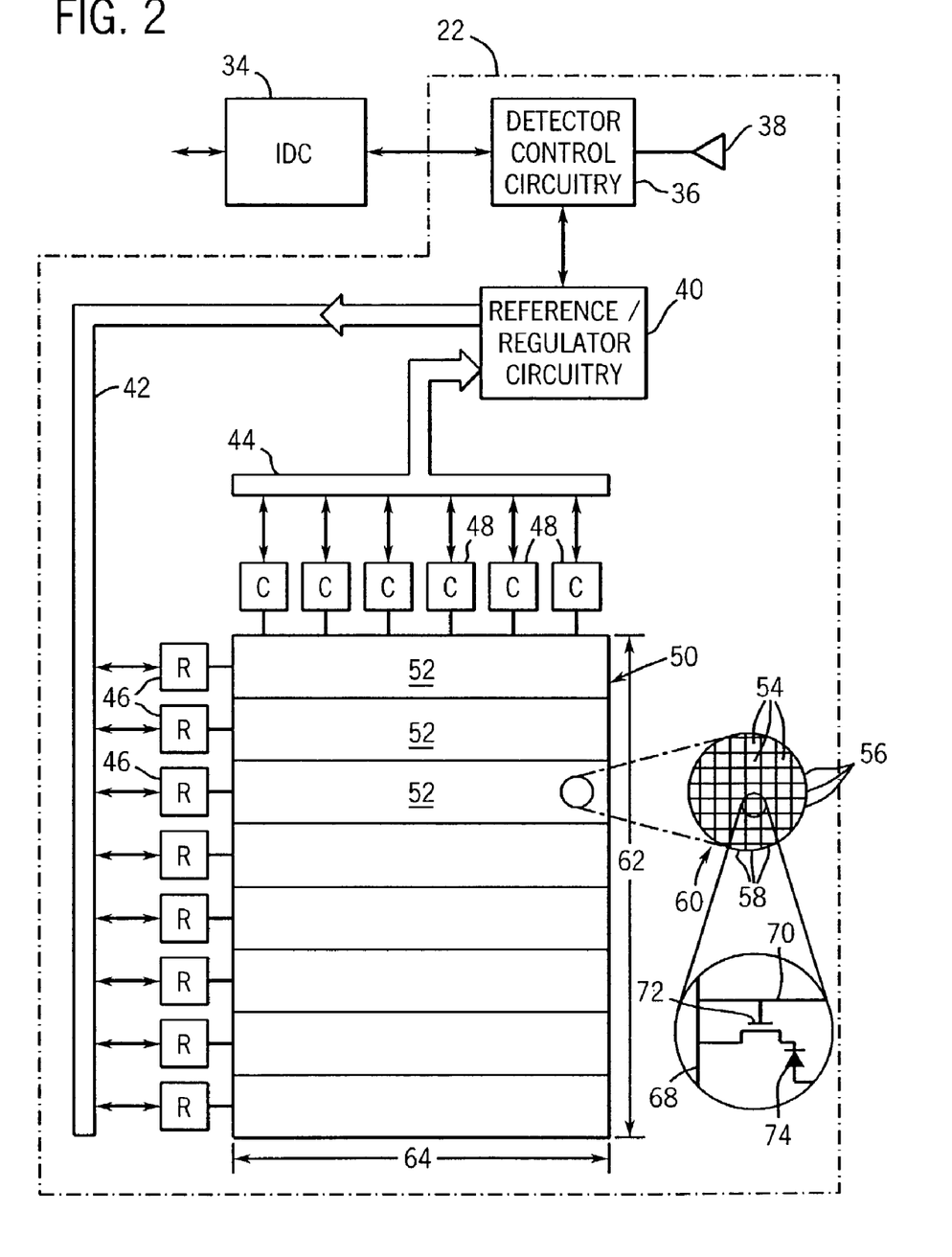
FIG. 2 is a diagrammatical representation of the functional circuitry in a detector of the system of FIG. 1 that is adapted to produce image data for reconstruction.

FIG. 2 is a diagrammatical representation of functional components of digital detector 22. FIG. 2 also represents an imaging detector controller or IDC 34, which will typically be configured within detector controller 26. IDC 34 includes a CPU or digital signal processor, as well as memory circuits for commanding acquisition of sensed signals from the detector. IDC 34 is coupled via two-way fiber optic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a present embodiment, detector 22 consists of a scintillator that converts X-ray photons received on the detector surface during examinations to lower energy (light) photons. An array of photo detectors then converts the light photons to electrical signals, which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. In a present form, the array of photo detectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector. In the present technique, the image acquisition rate is increased by employing a partial readout of the detector 22.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64. Again, as described below, the present technique allows an enhanced number of pixels to be read out via the row and column drivers and readout electronics.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode 74 may be accessed via readout electronics 48, and converted to digital signals for subsequent processing and image reconstruction. Thus, an entire row of pixels in the array is controlled simultaneously when the scan line attached to the gates of all the transistors of pixels on that row is activated. Consequently, each of the pixels in that particular row is connected to a data line, through a switch, which is used by the readout electronics to restore the charge to the photodiode 74.

It should be noted that as the charge is restored to all the pixels in one row simultaneously by each of the associated dedicated readout channels, the readout electronics is converting the measurements from the previous row from an analog voltage to a digital value. Furthermore, the readout electronics are transferring the digital values from two previous rows to the acquisition subsystem, which will perform some processing prior to displaying a diagnostic image on a monitor or writing it to film. Thus, the read out electronics are performing three functions simultaneously: measuring or restoring the charge for the pixels in a particular row, converting the data for pixels in the previous row, and transferring the converted data for the pixels in a twice previous row.

Figure 3:
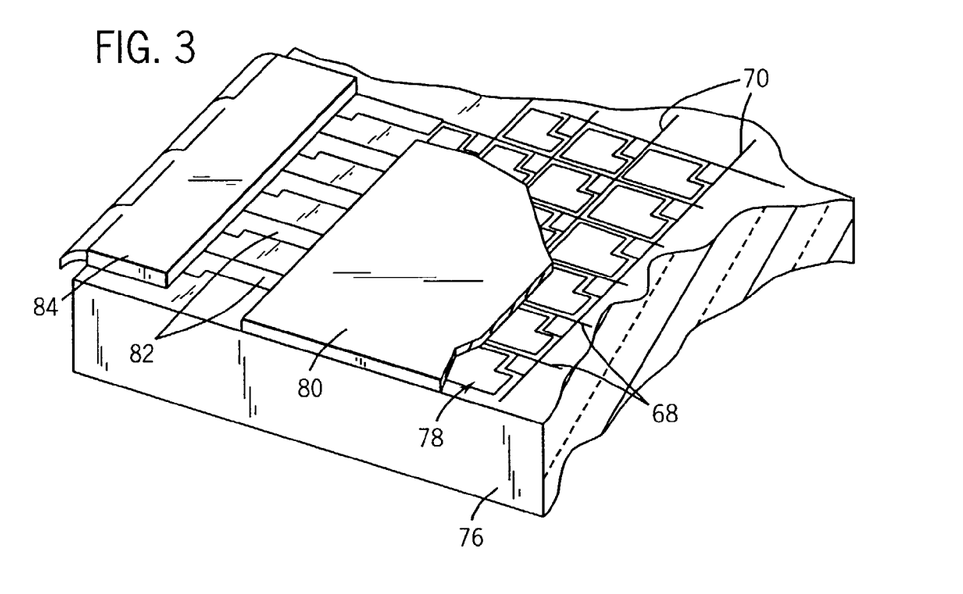
FIG. 3 is a partial sectional view illustrating an exemplary detector structure for producing the image data.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry.

It should be noted that the particular configuration of the detector panel 22, and the subdivision of the panel into rows and columns driven by row and column drivers is subject to various alternate configurations. In particular, more or fewer row and column drivers may be used, and detector panels having various matrix dimensions may thereby be defined. The detector panel 22 may be further subdivided into regions of multiple sections, such as along a vertical or horizontal centerline.

It should be further noted that the readout electronics in the detector generally employ a pipeline-type architecture. For example, as the charge is restored to all the pixels in a particular row simultaneously by each of the associated dedicated readout channels, the readout electronics convert the measurements from the previous row from an analog signal to a digital signal. Concurrently, the readout electronics transfer the measured digital values from two previous rows to the data acquisition subsystem. The data acquisition subsystem typically performs some processing prior to displaying a diagnostic image on a display. Thus, the readout electronics in the present technique perform three functions simultaneously.

Figure 4:
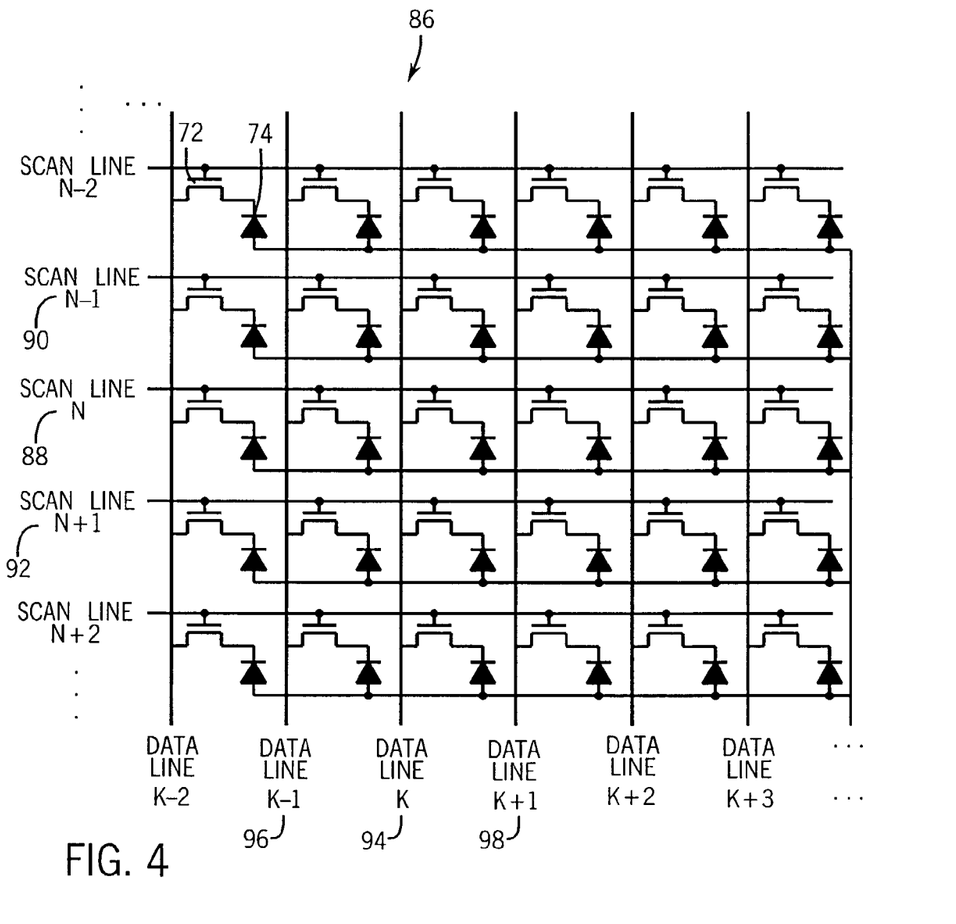
FIG. 4 is a circuit schematic illustrating rows and columns of pixels in an exemplary detector.

FIG. 4 illustrates an array of pixels 86 located on an exemplary detector having a plurality of column lines and row lines. As illustrated by the array of pixels 86, each pixel comprises the transistor 72 and the photodiode 74. It should be noted that the array is made up of a plurality of scan lines 88, 90, 92 and a plurality of data lines 94, 96 and 98. The scan lines 88, 90, 92 represent rows of pixels scanned during the imaging process. Similarly, the data lines 94, 96 and 98 represent the columns of pixels through which data is transmitted to a data acquisition system. As can be appreciated by those skilled in the art, the scan lines typically recharge the photodiode and measure the amount of charge displaced. The column or data lines typically transmit the data from each row of pixels to the data acquisition system.

As illustrated, scan line 88 (denoted N in FIG. 4) is coupled to each one of the pixels in that specific row. Additionally, scan line 88 is coupled to each of one of the data lines. For example, scan line 88 is coupled to data line 94 (denoted K in FIG. 4) and data line 98 (K+1). Similarly, each one of the data lines is coupled to each one of the scan lines. Thus, as illustrated for the array of pixels 86, scan line 88 (N), scan line 90 (N−1), and scan line 92 (N+1) are coupled to data line 94 (K), data line 96 (K−1), and data line 98 (K+1) and so on. It should be understood that each data line is typically coupled to one specific column of pixels and each scan line is coupled to one specific row of pixels. Additionally, although in the present embodiment of FIG. 4, 25 pixels are illustrated, it should be noted that additional pixels may, of course, be incorporated in the pixel array.

Figure 5:
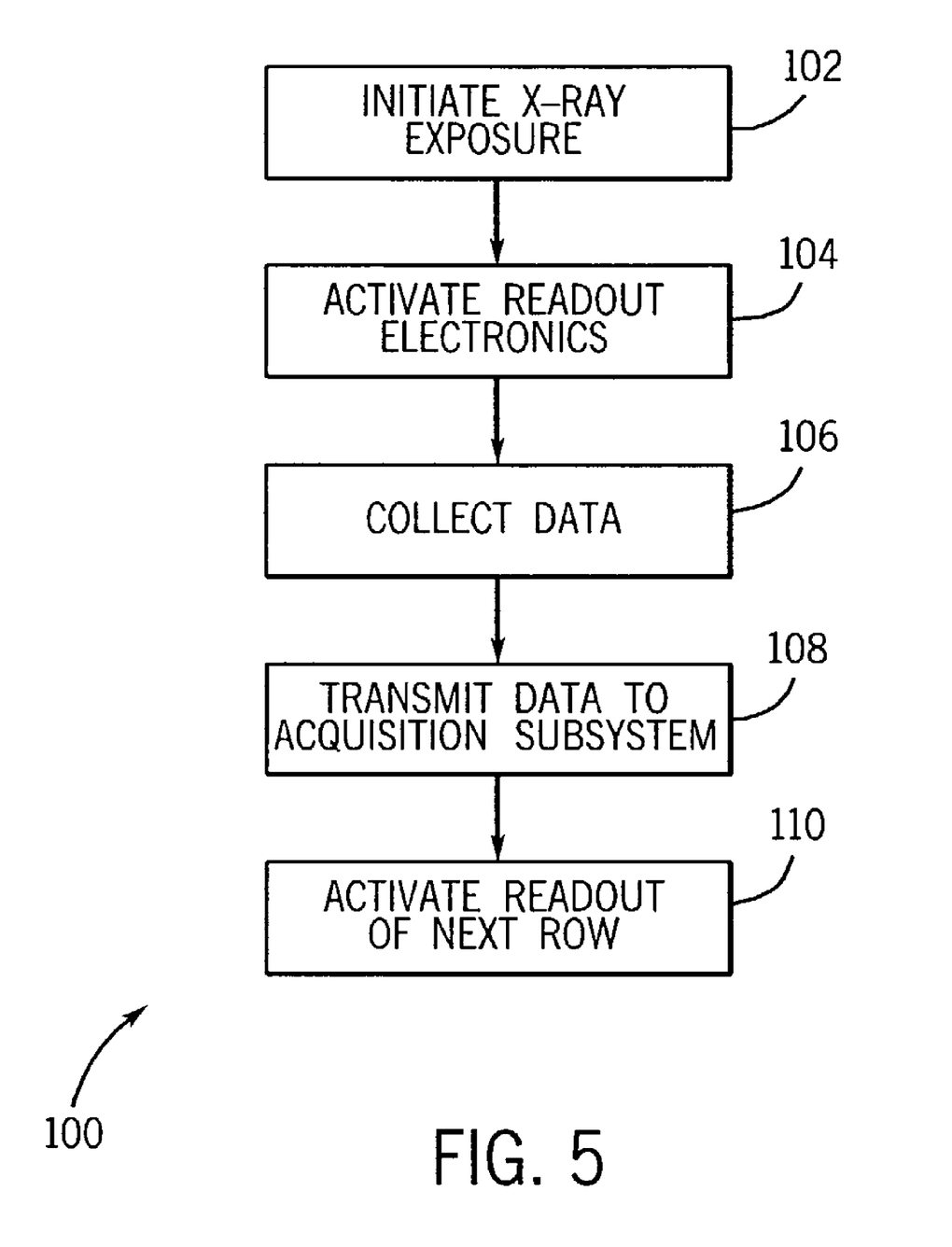
FIG. 5 is a flowchart representing a method of operating an exemplary imaging system for providing image data.

Turning to FIG. 5, a flowchart is represented illustrating a method 100 for operating an imaging system of the type described above. Initially, an X-ray exposure is initiated by an operator, as represented by step 102. Once an X-ray exposure is taken the readout electronics within the detector 22 are activated, as indicated by step 104. As mentioned above, an exposure is taken of a patient, whereby X-rays are transmitted through the patient and received by the detector. The array of pixels 86 typically measures the attenuation of the X-rays received by the detector 22, via the readout electronics provided within each individual pixel. The readout electronics typically collect data utilizing circuitry associated with each of the pixels, as indicated by step 106. Once the data are collected for a particular row of pixels, the data are transmitted to a data acquisition subsystem as indicated by step 108. Once data from one specific row of pixels is transmitted to the data acquisition subsystem, the next row of pixels is scanned and read. Thus, the readout of the next row of pixels is activated, as indicated by step 110. It should be understood that this process continues until the detector 22, and more particularly all the pixels, are read out. Subsequently, the collected data are processed and ultimately used to reconstruct an image of the exposure area.

Figure 6:
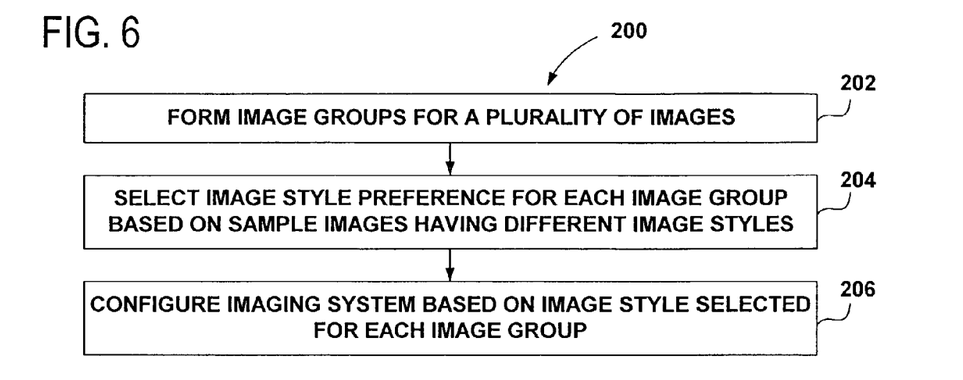
FIG. 6 is a flowchart illustrating an exemplary custom configuration process of the present technique.

As noted above, the present technique efficiently customizes the foregoing imaging system 10 based on preferred image styles, which are selected for each of a plurality of image subject matter groups. FIG. 6 is a flowchart illustrating an exemplary custom configuration process 200 of the present technique. As illustrated, the process 200 proceeds by forming image subject matter groups for a plurality of images (202). For example, imaging expertise, historical knowledge, statistical analysis, and experience with imaging subject matter may be used to select a plurality of core/representative image types/views, which are representative of all images typically produced with a certain imaging system/application. Each of the remaining image types/views may then be grouped with one of the core/representative image types/views based on a suitable relationship, such as a common subject matter of the images. For example, the process 200 may develop a mapping function for each of the remaining image types/views.

The process 200 then proceeds to select image style preferences for each image subject matter group based on sample images having different image styles (204). For example, the process 200 may display a sample image of each core/representative image type/view in each of the different image styles for review by the customer. The image style preferred by a customer for a particular core/representative image type/view is then used for each of the remaining image types/views grouped with that core/representative image type/view. The process 200 then proceeds to configure the imaging system based on the image style selected for each image subject matter group (block 206). For example, the process 200 may automatically configure operational parameters of the imaging system necessary to achieve each of the selected image styles for each image type/view grouped with a core/representative image type/view. The foregoing operational parameters may include system parameters affecting the image acquisition process, the processing of images acquired by the imaging system, or any other desired operational aspect of the imaging system.

Figure 7:
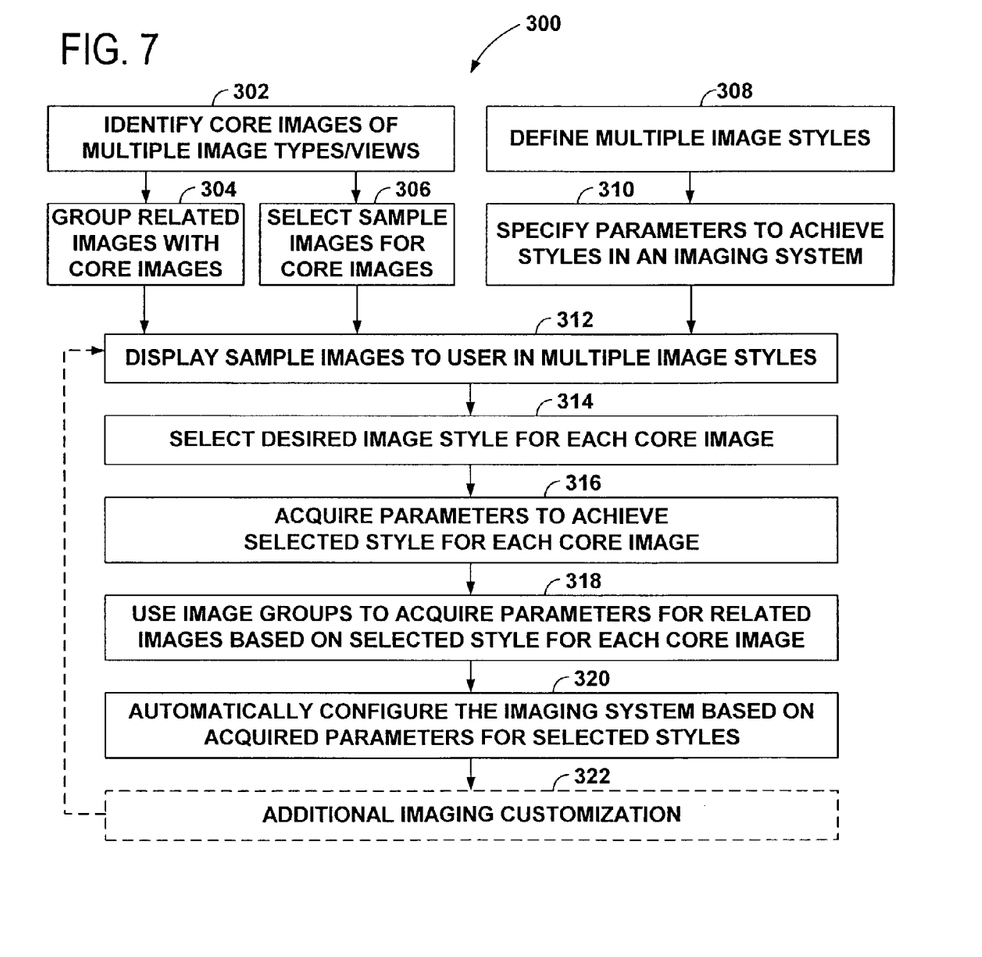
FIG. 7 is a flowchart illustrating an alternative customization process for an imaging system of the present technique.

FIG. 7 is a flowchart illustrating an alternative customization process 300 for an imaging system of the present technique. As illustrated, the process 300 proceeds by identifying core images of multiple image types/views (block 302). For example, the process 300 may use a variety of user/customer expertise, historical knowledge, statistical analysis, and knowledge/experience in the subject matter of the images to identify a plurality of core/representative image types/views. In medical imaging, the core/representative image types/views may correspond to core anatomical images/views, such as a representative view of a hand, an arm, a leg, a chest, a head, a heart, a lung, or any other desired anatomy. The process 300 then proceeds to group related images with core images (block 304). For example, each of the remaining image types/views may be grouped with one of the core/representative image types/views based on a suitable relationship, such as a common subject matter of the images. If no other image types/views are related with a particular core/representative image type/view, then the group is limited to the core/representative image type/view. In medical imaging, the process 300 may group all views of a particular anatomy with a core anatomical image, which is representative of the particular anatomy. The process 300 may organize the foregoing groups using a mapping function, a table, a spreadsheet, a database, or any other suitable organizational mechanism. Based on the foregoing groups and core/representative image types/views, the process 300 also selects at least one sample image for each core image type/view (block 306). For example, in medical imaging, a sample image may be collected/selected for each core anatomical image. If additional variables exist between potential images of the subject matter, then multiple sample images may be acquired to account for the variables. For example, a sample image may be collected/selected for a variety of patient sizes, such as a large patient anatomy, a small patient anatomy, and a medium patient anatomy.

The process 300 uses the foregoing core image types/views, groups, and sample core images to expedite configuration of the imaging system 10 in groups of common configuration preferences, as further illustrated in FIG. 7. Accordingly, the process 300 defines multiple image styles for all images generally associated with the imaging system (block 308). For example, the process 300 may use a variety of user/customer expertise, historical knowledge, statistical analysis, and knowledge/experience in the subject matter of the images to identify a plurality of image styles or looks expected by users/customers. The process 300 performs this style definition step for each system and application, such as each medical imaging system/modality. Each image style may comprise different image characteristics, such as different settings of contrast, brightness, edge characteristics, intensity, color depth, resolution, and any other characteristic associated with the image. The image styles also may have different video stream characteristics for a video image, audio stream characteristics for an audio stream for an image, and various other perceptible characteristics of the image. In medical imaging, the image styles may include a soft tissue enhanced image style, a bone enhanced image style, a specific organ enhanced image style, and various other desired styles. Based on the foregoing image styles, the process 300 then proceeds to specify parameters to achieve the image styles in a particular imaging system (block 310). For example, the process 300 may derive a set of operational parameters necessary to achieve each defined style for each of the plurality of image types/views typically associated with the imaging system. The process 300 may then organize the foregoing sets of operational parameters into one or more lookup tables, spreadsheets, databases, or other organizational structures for subsequent use upon user selection of the desired image style for each image subject matter group.

As illustrated in FIG. 7, the process 300 then proceeds to display the sample images to a user in the multiple image styles (block 312). The process 300 then facilitates selection of a desired image style for each core image (block 314). For example, after a customer has viewed the multiple image styles for a particular core image type/view as represented by the sample image, the customer may select one preferred style for the core image type/view and all related image types/views in the particular image subject matter group with that core image type/view. The selected image styles are then recorded and applied to the particular customer and imaging system/application. The process 300 proceeds by acquiring the operational parameters necessary to achieve the selected image style for each core image (block 316). For example, the process 300 may access and acquire the operational parameters from one or more lookup tables, which may include all operational parameters necessary to achieve all of the multiple image styles for all image types/views. The process 300 then proceeds to use the image subject matter groups defined in block 304 to identify and retrieve the appropriate operational parameters for all related image types/views based on the selected style for each core image (block 318). For example, the process 300 may use a mapping function for each core image to identify the grouped image types/views. The process 300 may then access the one or more lookup tables to acquire the operational parameters necessary to produce the preferred image style for each image type/view grouped with the core image. After the process 300 has acquired and recorded all the necessary operational parameters based on the image styles selected by the customer, the process 300 automatically configures the imaging system based on the acquired parameters for the selected styles (block 320). As noted above, the foregoing operational parameters may include system parameters affecting the image acquisition process, the processing of images acquired by the imaging system, or any other desired operational aspect of the imaging system. The process 300 also may provide a user interface for additional imaging customization at block 322. Moreover, the foregoing process of selecting preferred image styles may be repeated as necessary to achieve the desired imaging looks/styles for the particular customer and imaging system/application.

Figure 8:
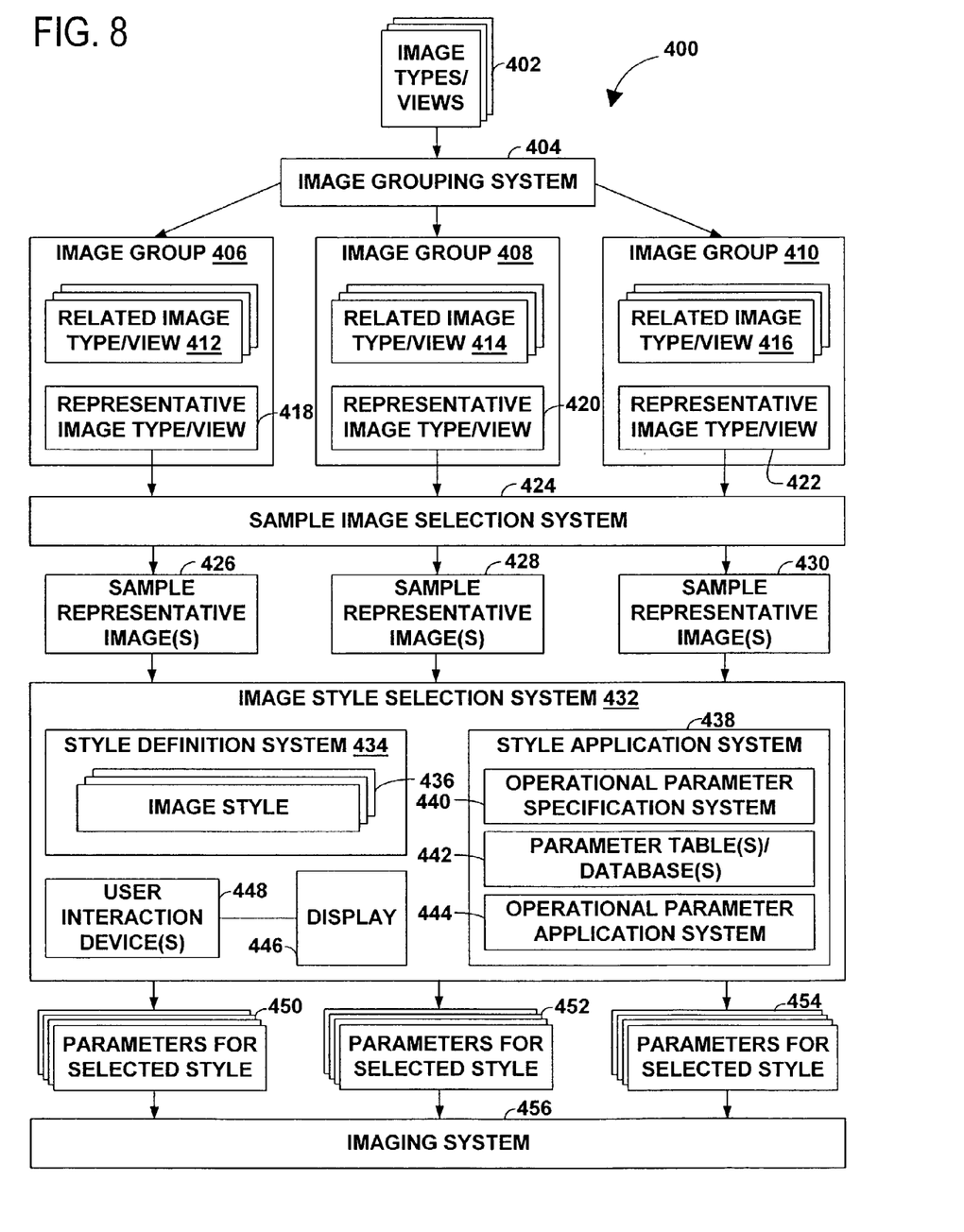
FIG. 8 is a block diagram illustrating an exemplary system for efficiently customizing an imaging system using image subject matter grouping and a number of preferred image styles.

FIG. 8 is a block diagram illustrating an exemplary system 400 for efficiently customizing an imaging system using image subject matter grouping and a number of preferred image styles. As illustrated, the system 400 has a plurality of image types/views 402, which are analyzed by an image subject matter grouping system 404. The image subject matter grouping system 404 uses a variety of user/customer expertise, historical knowledge, statistical analysis, and knowledge/experience in the subject matter of the image types/views 402 to form image subject matter groups, such as image subject matter groups 406, 408, and 410. The image subject matter grouping system 404 may comprise one or more computer systems, networks, informational databases, statistical analysis systems, customer feedback databases, and various other processing and informational resources. Moreover, the image subject matter grouping system 404 may include human resources, such as direct input from medical clinicians. As illustrated, the image subject matter grouping system 404 organizes multiple related image types/views 412, 414, and 416 with representative image types/views 418, 420, and 422 for each of the image subject matter groups 406, 408, and 410, respectively.

The illustrated system 400 also has a variety of systems to facilitate user selection of a desired image style for each of the image subject matter groups 406, 408, and 410. For example, the system 400 may include a sample image selection system 424 to collect/select sample images 426, 428, and 430 for the representative image types/views 418, 420, and 422, respectively. The sample image selection system 424 may use a variety of user/customer expertise, historical knowledge, statistical analysis, and knowledge/experience in the subject matter of the representative image types/views to identify, acquire, or otherwise gather sample images that are representative of the image types/views 418, 420, and 422, respectively. The sample image selection system 424 may comprise one or more computer systems, networks, picture archiving systems, informational databases, statistical analysis systems, customer feedback databases, and various other processing and informational resources. Again, multiple sample images may be acquired to account for image variations of a particular image type/view. For example, a sample image may be collected/selected for a variety of patient sizes, such as a large patient anatomy, a small patient anatomy, and a medium patient anatomy.

As illustrated in FIG. 8, the system 400 passes the sample representative image types/views 426, 428, and 430 to an image style selection system 432, which facilitates the user's selection of image styles to customize the imaging system to the user's preferences. The image style selection system 432 has a style definition system 434, which generates a plurality of image styles 436 based on user/customer expertise, historical knowledge, statistical analysis, and various other factors. The image style selection system 432 may include a wide variety of computer/network resources, informational databases, human resources, direct user input, and various other resources. Accordingly, the image styles 436 include a variety of different user-perceptible image characteristics, which may be expected for images produced by the imaging system. The image style selection system 432 also may have a style application system 438 to apply user-selected image styles to one or more desired imaging system/applications. Accordingly, the style application system 438 may include an operational parameter specification system 440, one or more parameter tables/databases 442, and an operational parameter application system 444. The operational parameter specification system 440 may generate operational parameters necessary to achieve each of the defined image styles 436 for each of the plurality of image types/views 402 for each imaging system/application. The style application system 438 then organizes and stores these operational parameters in the one or more parameter tables/databases 442. The operational parameter application system 444 facilitates the retrieval, delivery, and insertion of the appropriate operational parameters from the parameter tables/databases 442 to the desired imaging system/application.

The image style selection system 432 also may have one or more displays 446 to facilitate the display of the sample images 426, 428, and 430 in each of the various image styles 436. Moreover, one or more user interaction devices 448 may be provided to allow the user to select a preferred style for each of the representative image types/views 418, 420, and 422, as illustrated by the multiple image styles 436 displayed for each of the sample images 426, 428, and 430, respectively. Accordingly, the image style selection system 432 records a user-selected image style for each of the representative image types/views 418, 420, and 422. The style application system 438 then acquires parameters 450 for the representative image type/view 418 and each of the related image types/views 412 based on the selected image style from image styles 436. The style application system 438 also acquires parameters 452 for the representative image type/view 420 and each of the related image types/views 414 based on the selected image style from image styles 436. The style application system 438 further acquires parameters 454 for the representative image type/view 422 and each of the related image types/views 416 based on the selected image style from image styles 436. Each of these parameter sets 450, 452, and 454 are then transmitted to and configured into the imaging system, such as imaging system 456.

Figure 9:
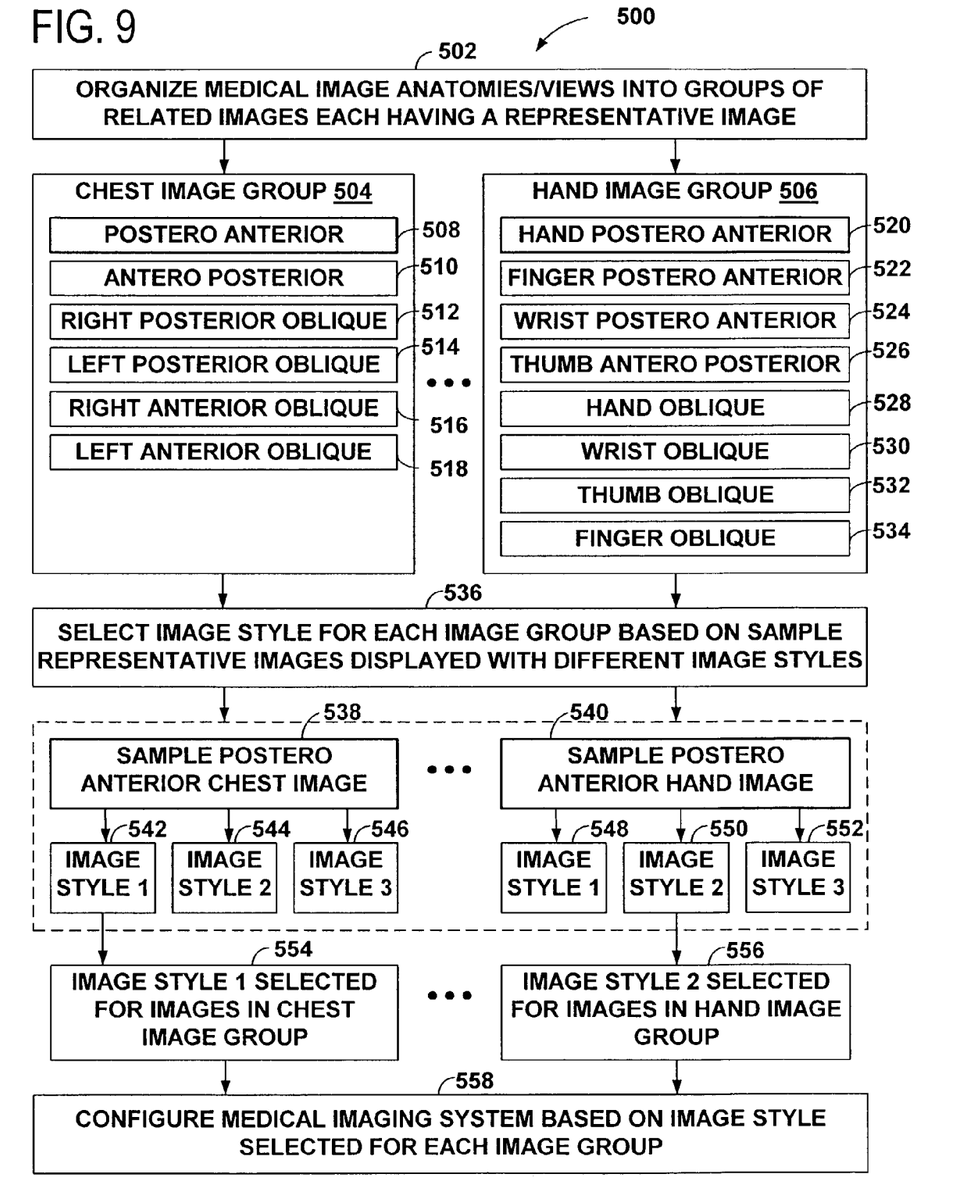
FIG. 9 is a flowchart illustrating an exemplary medical imaging customization process of the present technique.

FIG. 9 is a flowchart illustrating an exemplary medical imaging customization process 500 of the present technique. As illustrated, the process 500 proceeds by organizing medical image anatomies/views into groups of related images each having a representative image (502). For example, the process 500 may use a variety of medical imaging expertise, clinical expertise in a medical field, historical medical knowledge, statistical analysis of factors such as customer feedback, and experience with the medical/imaging subject matter to organize a plurality of anatomical groups, such as a chest image subject matter group 504 and a hand image subject matter group 506. In the illustrated embodiment, the chest group 504 includes a variety of related chest image views, such as a postero anterior view 508, an antero posterior view 510, a right posterior oblique view 512, a left posterior oblique view 514, a right anterior oblique view 516, and a left anterior oblique view 518. Similarly, the hand group 506 includes a variety of related hand image views, such as a hand postero anterior view 520, a finger postero anterior view 522, a wrist postero anterior view 524, a thumb postero anterior view 526, a hand oblique view 528, a wrist oblique view 530, a thumb oblique view 532, and a finger oblique view 534. In each of these groups 504 and 506, the process 500 also selects one image anatomy/view as the representative image anatomy/view. In the illustrated embodiment, the postero anterior view 508 is the representative image anatomy/view for the chest group 504, while the hand postero anterior view 520 is the representative image anatomy/view for the hand group 506.

After forming the groups 504 and 506, the process 500 proceeds to select an image style for each image subject matter group based on sample representative images displayed with different image styles (block 536). Accordingly, the process 500 displays a sample postero anterior chest image 538 in a variety of predefined image styles, such as image styles 1, 2 and 3 referenced by numerals 542, 544, and 546. The sample postero anterior chest image 538 corresponds to the postero anterior view 508, which the process 500 identified as the representative view for the chest image subject matter group 504. The process 500 repeats this display and selection process for each image subject matter group organized in block 502. Accordingly, the process 500 displays a sample postero anterior hand image 540 in a variety of predefined image styles, such as image styles 1, 2 and 3 referenced by numerals 548, 550, and 552. The sample postero anterior hand image 540 corresponds to the hand postero anterior view 520, which the process 500 identified as the representative view for the hand image subject matter group 506. As indicated by reference numerals 554 and 556, the customer selected image style 1 for images in the chest image subject matter group 504 and image style 2 for images in the hand image subject matter group 506. The process 500 then proceeds to configure the medical imaging system based on the image style selected for each image subject matter group (block 558). As mentioned above, the process 500 may automatically customize the medical imaging system based on the foregoing image preferences by accessing parameter lookup tables and acquiring the appropriate parameters for the selected image styles.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An imaging method, comprising the acts of:
   forming a plurality of core groups of image subject matter based at least partially on expertise in the image subject matter;
   facilitating selection of imaging preferences for each of the core groups based on multiple appearance styles of a sample image for each of the core groups;
   mapping each of a plurality of non-core groups of image subject matter to one group of the core groups, such that each non-core group is associated with the imaging preferences of the one group; and
   configuring an imaging system based on the imaging preferences.

2. The imaging method of claim 1, wherein the act of forming the plurality of core groups comprises the act of identifying a plurality of core images representative of different anatomies of a subject.

3. The imaging method of claim 1, wherein the act of facilitating selection of imaging preferences comprises the act of providing the multiple appearance styles of the sample image for each of the core groups based on different image acquisition parameters.

4. The imaging method of claim 1, wherein the act of facilitating selection of imaging preferences comprises the act of providing the multiple appearance styles of the sample image for each of the core groups based on different image processing parameters.

5. The imaging method of claim 1, wherein the act of facilitating selection of imaging preferences comprises the act of providing a user option between different still image appearances in the multiple appearance styles of the sample image for each of the core groups.

6. The imaging method of claim 1, wherein the act of facilitating selection of imaging preferences comprises the act of providing a user option between different video stream characteristics in the multiple appearance styles of the sample image for each of the core groups.

7. The imaging method of claim 1, wherein the act of facilitating selection of imaging preferences comprises the act of defining the multiple appearance styles.

8. The imaging method of claim 7, wherein the act of defining the multiple appearance styles comprises the act of analyzing customer feedback.

9. The imaging method of claim 7, wherein the act of defining the multiple appearance styles comprises the act of tailoring the multiple appearance styles to visual expectations of medical clinicians.

10. The imaging method of claim 7, wherein the act of defining the multiple appearance styles comprises the act of characterizing brightness, contrast, sharpness, and edge characteristics.

11. The imaging method of claim 7, wherein the act of defining the multiple appearance styles comprises the act of characterizing video stream characteristics.

12. The imaging method of claim 7, wherein the act of defining the multiple appearance styles comprises the act of specifying system parameters necessary to achieve the multiple appearance styles for each image in the core group.

13. The imaging method of claim 1, wherein the act of configuring the imaging system comprises the act of setting operational parameters of the imaging system to achieve the imaging preferences for each of the core groups.

14. The imaging method of claim 1, wherein the act of configuring the imaging system comprises the act of automatically setting image acquisition parameters of the imaging system.

15. The imaging method of claim 1, wherein the act of configuring the imaging system comprises the act of automatically setting image processing parameters of the imaging system.

16. The imaging method of claim 1, wherein the act of configuring the imaging system comprises the act of customizing the imaging system to the imaging preferences of a particular user.

17. An imaging method, comprising the acts of:
   forming a plurality of image subject matter groups each having a representative image;
   defining multiple image looks based at least partially on expertise, wherein the multiple image looks comprise a soft tissue enhanced image look, a bone enhanced image look, a specific organ enhanced image look, or a combination thereof;
   specifying imaging system parameters necessary to achieve the multiple image looks;
   providing an option to select a desired image look from the multiple image looks for each representative image; and
   facilitating use of the imaging system parameters to achieve the desired image look for the corresponding representative image and each related image in a corresponding group of the plurality of image subject matter groups.

18. The imaging method of claim 17, wherein the act of forming the plurality of image subject matter groups comprises the act of grouping image types/views based on feedback from users of an imaging system.

19. The imaging method of claim 17, wherein the act of forming the plurality of image subject matter groups comprises the act of grouping related medical images based on clinical expertise.

20. The imaging method of claim 17, wherein the act of defining the multiple image looks comprises the act of analyzing historical characteristics of images produced by an imaging system.

21. The imaging method of claim 17, wherein the act of defining the multiple image looks comprises the act of tailoring the multiple image looks to image appearance characteristics expected by medical clinicians.

22. The imaging method of claim 17, wherein the act of defining the multiple image looks comprises the act of varying still image characteristics.

23. The imaging method of claim 17, wherein the act of specifying imaging system parameters comprises the act of identifying image acquisition parameters necessary to acquire images having the multiple image looks for each image in each of the plurality of image subject matter groups.

24. The imaging method of claim 17, wherein the act of specifying imaging system parameters comprises the act of identifying image processing parameters necessary to process images having the multiple image looks for each image in each of the plurality of image subject matter groups.

25. The imaging method of claim 17, wherein the act of specifying imaging system parameters comprises the act of generating operational parameters for a particular imaging system.

26. The imaging method of claim 17, wherein the act of specifying imaging system parameters comprises the act of acquiring operational parameters for an imaging system in a particular medical modality.

27. The imaging method of claim 17, wherein the act of providing the option to select the desired image look comprises the act of displaying the multiple image looks with a sample image for each representative image.

28. The imaging method of claim 27, wherein the act of providing the option to select the desired image look further comprises the act of requesting a user to select the desired image look based on the multiple image looks displayed with each sample image 29. The imaging method of claim 17, wherein the act of facilitating use of the imaging system parameters comprises the act of configuring an imaging system to acquire images having the desired image looks.

30. The imaging method of claim 17, wherein the act of facilitating use of the imaging system parameters comprises the act of configuring an imaging system to process images to have the desired image looks.

31. The imaging method of claim 17, wherein the act of providing the option to select the desired image look comprises acquiring a selection of the desired image look from the multiple image looks for each of the image subject matter groups corresponding to an anatomy of a subject, and wherein the act of facilitating use of the imaging system parameters to achieve the desired image look comprises configuring the imaging system based on the desired image look corresponding to the anatomy of the subject for each of the image subject matter groups.

32. An imaging method, comprising the acts of:
  means for grouping a plurality of images into groups of related images based on different anatomies of a subject; and
  means for configuring an imaging system to facilitate a desired image look based on a preference from different appearance styles for each of the groups of related images, wherein the different appearance styles comprise different internal image enhancements of features inside the subject.

33. The imaging method of claim 32, comprising means for characterizing a plurality of image styles.

34. The imaging method of claim 32, comprising means for deriving operational parameters of the imaging system necessary to facilitate the desired image looks.

35. The imaging method of claim 32, comprising means for setting operational parameters of the imaging system to facilitate the desired image looks.

36. The imaging method of claim 32, wherein the means for configuring the imaging system comprises using the preference based at least partially on different video stream characteristics in the different appearance styles.

37. A computer readable medium encoded with computer readable code, comprising:
  an image mapping routine configured to organize image types/views into a plurality of image subject matter groups based at least partially on expertise in subject matter of the images;
  an image style selection routine configured to facilitate user selection of imaging preferences for each of the plurality of image subject matter groups based on sample images having different image appearance styles representative of a particular anatomy of a subject, wherein the different image appearance styles comprise different variations of features inside the subject; and
  a system configuration routine for configuring an imaging system based on the imaging preferences.

38. The computer readable medium of claim 37, wherein the image mapping routine comprises an image associating routine for associating each of the images with a related one of a plurality of core images representative of related subject matter.

39. The computer readable medium of claim 37, wherein the image style selection routine comprises a style definition routine for defining a plurality of different image looks.

40. The computer readable medium of claim 37, wherein the system configuration routine comprises an automation routine for automatically executing the system configuration routine upon user selection of the imaging preferences.

41. The computer readable medium of claim 37, wherein the image style selection routine includes a user option between different video stream characteristics in the different image appearance styles.

42. A system for customizing an imaging system, comprising:
  at least one machine readable medium storing a plurality of image styles, a plurality of image subject matter groups each having a representative image type based on an anatomy of a subject, and a sample image for each representative image type;
  a style selection interface adapted to display each sample image in each of the plurality of image styles to facilitate user selection of a preferred style from the plurality of image styles for each representative image type illustrated by the respective sample image based on the anatomy of the subject, wherein the plurality of image styles comprises various enhancements of features inside the subject; and
  a style configuration system adapted to configure operational parameters of an imaging system to achieve the preferred style for each respective group of the plurality of image subject matter groups based on the anatomy of the subject.

43. The system of claim 42, wherein the plurality of image styles comprise different contrast, brightness, and edge characteristics.

44. The system of claim 42, wherein the plurality of image styles comprise different anatomical accentuations for medical diagnostic images.

45. The system of claim 42, wherein the plurality of image subject matter groups comprise different anatomical categories.

46. The system of claim 45, wherein each group of the plurality of image subject matter groups comprises different views of an anatomy.

47. The system of claim 42, wherein the operational parameters comprise image processing parameters.

48. The system of claim 42, wherein the operational parameters comprise image acquisition parameters.

49. The system of claim 42, wherein the style configuration system is applicable to multiple types of imaging systems in different medical modalities.

50. The system of claim 42, wherein at least one group of the plurality of image subject matter groups has only the representative image type.

51. The system of claim 42, wherein the style selection interface includes a user option between different video stream characteristics in the plurality of image styles.

52. An imaging method, comprising the acts of:

forming image subject matter groups based at least partially on expertise in subject matter of the images, wherein the image subject matter groups represent a plurality of different anatomical parts including different internal features of a subject;

facilitating selection of imaging preferences for each of the image subject matter groups based on multiple appearance styles of a sample image for each of the image subject matter groups, wherein each sample image is representative of a different one of the different anatomical parts of the subject; and configuring an imaging system based on the imaging preferences.

53. An imaging method, comprising the acts of:

forming image subject matter groups based at least partially on expertise in subject matter of the images;

facilitating selection of imaging preferences for each of the image subject matter groups based on multiple appearance styles of a sample image for each of the image subject matter groups, wherein the multiple appearance styles are associated with different settings including different image acquisition settings, wherein the image subject matter groups represent a plurality of different anatomical parts including different internal features of a subject; and configuring an imaging system based on the imaging preferences.

54. A method, comprising:

selecting a plurality of core groups of different anatomies of a subject;

mapping each of a plurality of non-core groups to one of the plurality of core groups;

presenting a plurality of different image styles of a sample image for each of the plurality of core groups, but not for the plurality of non-core groups;

obtaining a user selection of one of the plurality of different image styles of the sample image for each of the plurality of core groups, but not for the plurality of non-core groups; and setting parameters of an image system to output images with the user selection corresponding to each core group and each non-core group mapped to the respective core group.

55. The method of claim 54, wherein the plurality of different anatomies comprise internal anatomical parts of the subject.

56. The method of claim 54, wherein the plurality of different anatomies comprise a hand, an arm, a leg, a chest, a head, a heart, a lung, or a combination thereof.

57. The method of claim 54, wherein the plurality of different image styles comprise enhancements to bone tissue, soft tissue, organs, or a combination thereof.

58. The method of claim 54, comprising imaging the subject according to the parameters.

* * * * *